United States Patent
Bouanani et al.

(10) Patent No.: US 6,929,924 B2
(45) Date of Patent: Aug. 16, 2005

(54) C-PEPTIDE SPECIFIC ASSAY PROCEDURE (75) Inventors: Majida Bouanani, Douglas (GB); Nadia Kamal, Lyons (FR); Catherine Christianne Marie Larue, Vaucresson (FR); Bernard Christian Pau, Montpellier (FR); Elisabeth Siohan, Millery (FR)

(73) Assignee: Pasteur Sanofi Diagnostics, Marnes la Coquette (FR)

( * ) Notice: Subject to any disclaimer, the term of this patent is extended or adjusted under 35 U.S.C. 154(b) by 0 days.

(21) Appl. No.: 10/792,395

(22) Filed: Mar. 4, 2004

(65) Prior Publication Data

US 2005/0037448 A1 Feb. 17, 2005

Related U.S. Application Data (63) Continuation of application No. 09/446,360, filed as application No. PCT/FR98/01253 on Jun. 15, 1998, now abandoned.

(30) Foreign Application Priority Data

Jun. 20, 1997 (FR) .............................................. 97 07730

(51) Int. Cl.⁷ .................... G01N 33/543; G01N 33/577; G01N 33/74; C07K 16/26; C12P 21/08
(52) U.S. Cl. .................... 435/7.92; 435/7.93; 435/7.94; 435/70.21; 435/331; 435/336; 435/962; 435/975; 436/518; 436/536; 436/548; 530/387.9; 530/388.24; 530/389.2; 530/845
(58) Field of Search ............................. 435/7.92, 7.93, 435/7.94, 70.21, 331, 336, 975, 962; 436/518, 536, 548; 530/387.9, 388.24, 389.2, 845

(56) References Cited

U.S. PATENT DOCUMENTS 4,722,889 A  2/1988  Lee et al. ...................... 435/7
5,026,653 A  6/1991  Lee et al. ................... 435/7.94
5,914,241 A  6/1999  Valkirs ....................... 435/7.92

FOREIGN PATENT DOCUMENTS

EP    0484961 A1   5/1992

OTHER PUBLICATIONS

Dinesen et al., First assay specific for intact human proinsulin. Diabetologia 37 (Suppl. 1): A103, Abstract #400.*

Madsen et al., 1984. Human proinsulin–specific antigenic determinants identified by monoclonal antibodies. Diabetes 33:1012–1016.

Hellstrom et al., 1985. In *Monoclonal Antibodies for Cancer Detection and Therapy* (Baldwin et al, eds.), Academic Press, London. p. 20.

Madsen et al., "The Production and Characterization of Monoclonal Antibodies Specific for Human Proinsulin Using a Sensitive Microdot Assay Procedure," *Endochrinology*, 113(6):2135–2144 (1983).

Angelo et al., "A Highly Sensitive Monoclonal Antibody Against Human C–Peptide," *Diabetes Research and Clinical Practice*, vol. Suppl. 1:S18–S19 (1985).

Reaven et al., "Plasma Insulin, C–Peptide, and Proinsulin Concentrations in Obese and Nonobese Individuals with Varying Degrees of Glucose Tolerance," *Journal of Clinical Endocrinology and Metabolism*, 76(1):44–48 (1993).

\* cited by examiner

Primary Examiner—Christopher L. Chin
Assistant Examiner—James L. Grun
(74) Attorney, Agent, or Firm—Jacobson Holman PLLC (57) ABSTRACT

The present invention relates to a specific C-peptide assay method which can eliminate all interference due to proinsulin and its intermediates, in particular des-31,32-proinsulin and/or des-64,65-proinsulin. It also relates to antibodies for carrying out this assay.

12 Claims, 3 Drawing Sheets

```
                        SEQUENCE LISTING

<160> NUMBER OF SEQ ID NOS: 6

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Gly Ala Gly Ser Leu Gln Pro Leu Ala Leu Glu Gly Ser
 1               5                  10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Pro Lys Thr Arg Arg Glu Ala Glu Asp Leu Gln Val
 1               5                  10

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Gln Lys Arg Gly Ile Val Glu
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued

```
          peptide

<400> SEQUENCE: 4

Leu Gln Lys Arg Gly Ile Val Glu Gln
  1               5

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
          peptide

<400> SEQUENCE: 5

Phe Tyr Thr Pro Lys Thr Arg Arg Glu Ala Glu Asp Leu Gln Val
  1               5                  10                  15

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
          peptide

<400> SEQUENCE: 6

Phe Tyr Thr Pro Lys Thr Arg Arg Glu Ala Glu Asp Leu
  1               5                  10
```

C-PEPTIDE SPECIFIC ASSAY PROCEDURE

This is a continuation of application Ser. No. 09/446,360 filed Jul. 19, 2000 now abandoned, which is a 371 of application No. PCT/FR98/012534, filed Jun. 15, 1998, and published in French, the disclosures of the foregoing being incorporated by reference herein.

The present invention relates to a specific C-peptide assay method which can eliminate all interference due to proinsulin and its intermediates, in particular des-31,32-proinsulin and/or des-64,65-proinsulin. It also relates to antibodies for carrying out this assay.

Insulin is synthesised in the β cells of Langerhans islets from a precursor, proinsulin. Proinsulin is acted on by proteolytic enzymes which detach insulin (molecular mass 5800 Daltons) and C-peptide (molecular mass 3020 Daltons) from it. The hydrolysis uses two types of proteases, one of a carboxypeptidase type and the other of a endopeptidase type. The process involves intermediate compounds such as split-32,33-proinsulin, split-65,66-proinsulin, des-31,32-proinsulin and des-64,65-proinsulin, which with intact proinsulin subsist in small proportions (2% to 6%) alongside insulin and C-peptide.

The equimolar ratio of portal insulin and C-peptide is not reflected at the peripheral level. In venous peripheral blood in the basal state, on average there is 3 to 6 times more C-peptide than insulin. This phenomenon can be explained by the differences in metabolism between those two polypeptides. About 50% of the insulin is inactivated on passing through the liver. The remaining amounts are inactivated in its peripheral receptors, mainly present in muscular or adipose tissue. In contrast, C-peptide has practically free passage through the liver and therefore has a much longer plasmic half-life than insulin (30 minutes for the C-peptide and less than 5 minutes for insulin). The C-peptide does not have any known biological action. Its role is limited to folding the proinsulin molecule in the β cells of the pancreas. It appears as a simple residue in the vascular sector before being eliminated intact by the kidneys.

Plasmic or urinary assay of C-peptide thus constitutes a means of evaluating insulin secretion which is far more reliable than insulin assay. C-peptide assay enables endogenous insulin production to be estimated, even during administration of exogenous insulin to a patient or in the presence of anti-insulin antibodies which do not permit direct immunological insulin assay.

C-peptide assay is of particular application for differential diagnosis of type I diabetes and type II diabetes, in evaluating the residual pancreatic function of the β cells, in detecting and monitoring the remission phase in type I diabetes, in detecting artificial hypoglycemia caused by insulin injection, in diagnosing insulinomas and in evaluating insulin secretion during liver disease.

C-peptide assay is also used to establish a diabetes prognosis for the foetus when monitoring pregnancy in diabetic women. Further, C-peptide is measured when monitoring total pancreatectomy.

C-peptide assay methods are known. Patent application EP 227351 describes the use of an anti-C-peptide antiserum to measure C-peptide in competitive radioimmunological assay. Anti-C-peptide monoclonal antibodies for use in radioimmunological tests have also been described by Angelo et al. (Diabetes Research and Clinical Practice (1985) vol. suppl. 1, p. 18–19). As in the preceding case, the antibodies are used in competitive immunoassay. Further, Madsen et al., (Endocrinology (1983) 113, No. 6, pp. 2135–2144) have described the production and characterisation of monoclonal antibodies which are specific to human proinsulin. Application EP 484961 describes a "sandwich" type method for C-peptide detection and assay which can be carried out using monoclonal or polyclonal antibodies. The C-peptide can be evaluated using ELISA, for example.

Patent CS 277597 published 17th Mar. 1993 also describes the use of monoclonal antibodies for proinsulin or C-peptide assay.

Almost all anti-C-peptide monoclonal or polyclonal antibodies are known to cross react to a greater or lesser extent with proinsulin and the intermediate forms produced before cleavage into insulin and C-peptide. Polyclonal or monoclonal antibodies produced from C-peptide alone can recognise C-peptide in proinsulin and in the intermediate forms produced before cleavage into insulin and C-peptide because free C-peptide and C-peptide bound to insulin which forms proinsulin are very similar.

In a normal subject, C-peptide concentrations are about 50 times higher than those of proinsulins (about 0.5–1.5 nM as opposed to 5–25 pM fasting). However, in some cases of NIDD (non-insulin dependent diabetes), in newly diagnosed type I diabetics and in their family, during insulinoma and in familial hyperproinsulinemia, the plasmic concentrations of proinsulins are increased and may exceed 2000 pM. In such situations, the principal forms present in the blood are intact proinsulin and des-31,32-proinsulin. The other intermediates are present in circulating blood only in minute quantities (Reaven et al., J. Clin. Endocrinol. Metabol. (1993), 1, pp. 44–48).

It is thus important to use specific methods for evaluating C-peptide which can eliminate interference due to intact proinsulin and des-31,32-proinsulin to provide a reliable result in any pathophysiological situation. Dinesens et al. ("First assay specific for intact human proinsulin", communication given at EASD'94 30th annual meeting, Düsseldorf, 27th Sep.–1st Oct. 1994) have proposed an assay specific to proinsulin—without interference due to insulin— using two antibodies specific to the AC junction (junction between the A chain of the insulin and the C-peptide) and the BC junction (junction between the B chain of the insulin and the C-peptide) in proinsulin. However, those authors have not proposed a specific C-peptide assay which could eliminate interference due to proinsulins.

The use of specific antibodies ("scavenger antibodies") to eliminate interference due to the presence of related biological substances has already been described in the prior art. For example, U.S. Pat. No. 4,722,889 describes a sandwich type assay method specific to human chorionic gonadotropin (hCG) using two antibodies which can also recognise thyroid stimulating hormone (TSH), follicle stimulating hormone (FSH) and luteinizing hormone (LH). To eliminate interference due to the last three hormones, a third scavenging antibody which specifically recognises the epitope of the β unit of TSH, FSH and LH and which has a lower affinity for the β unit of hCG is used. Further, when the interfering antigen is in excess, the non-specific antibody of the solid phase is saturated and thus the antibodies to be assayed are under-evaluated. In contrast, nowhere in the prior art is it stated that in order to obtain a specific assay it is possible to use an antibody which recognises the substance to be assayed as well as the precursor of the substance considered to be interfering. It is then possible to envisage all types of assay, including a competitive type assay.

BRIEF SUMMARY OF THE INVENTION

The applicant has now discovered a specific C-peptide assay method which can eliminate all interference due to des-31,32-proinsulin and/or des-64,65-proinsulin. Due to the use of specific antibodies for intact proinsulin, for des-31,32-proinsulin and/or for des-64,65-proinsulin, recognising an epitope adjacent the epitope of the anti-C-peptide antibody, it is possible to carry out highly accurate C-peptide assays in biological media with high specificity.

DETAILED DESCRIPTION OF THE INVENTION

The invention concerns a C-peptide assay method in which a sample which may contain C-peptide is brought into contact with one or more anti-C-peptide antibodies and an anti-proinsulin antibody which is specific to intact proinsulin and des-31,32-proinsulin, recognising an epitope which is either adjacent or overlaps the epitope of the anti-C-peptide antibody, thus interfering with binding of the anti-C-peptide antibody to intact proinsulin and des-31,32-proinsulin, or an anti-proinsulin antibody which is specific to intact proinsulin and des-64,65-proinsulin, recognising an epitope which is either adjacent or overlaps the epitope of the anti-C-peptide antibody, thus interfering with binding of the anti-C-peptide antibody to intact proinsulin and des-64,65-proinsulin, or a mixture of said anti-proinsulin antibody which is specific to intact proinsulin and des-31,32-proinsulin and said anti-proinsulin antibody which is specific to intact proinsulin and des-64,65-proinsulin.

In a particular implementation of the invention, a sample which may contain C-peptide is brought into contact:
either with an anti-C-peptide antibody and an anti-proinsulin antibody which is specific to intact proinsulin and des-31,32-proinsulin, recognising an epitope which is either adjacent or overlaps the epitope of the anti-C-peptide antibody, thus interfering with binding of the anti-C-peptide antibody to intact proinsulin and des-31,32-proinsulin, or an anti-proinsulin antibody which is specific to intact proinsulin and des-64,65-proinsulin, recognising an epitope which is either adjacent or overlaps the epitope of the anti-C-peptide antibody, thus interfering with binding of the anti-C-peptide antibody to intact proinsulin and des-64,65-proinsulin, or with a mixture of a first anti-C-peptide antibody and an anti-proinsulin antibody which is specific to intact proinsulin and des-31,32-proinsulin, recognising an epitope which is either adjacent or overlaps the epitope of said first anti-C-peptide antibody, thus interfering with binding of the anti-C-peptide antibody to intact proinsulin and des-31,32-proinsulin, and a second anti-C-peptide antibody and an anti-proinsulin antibody which is specific to intact proinsulin and des-64, 65-proinsulin, recognising an epitope which is either adjacent or overlaps the epitope of said second anti-C-peptide antibody, thus interfering with binding of said second anti-C-peptide antibody to intact proinsulin and des-64,65-proinsulin;

said first and said second anti-C-peptide antibodies optionally being identical.

When said first and said second anti-C-peptide antibodies are identical, a sample which may contain C-peptide is brought into contact with an anti-C-peptide antibody, an anti-proinsulin antibody specific to intact proinsulin and des-31,32-proinsulin, and an anti-proinsulin antibody specific to intact proinsulin and des-64,65-proinsulin.

In a preferred implementation of the invention, said epitope recognised by the antibody which is specific to intact proinsulin and des-31,32-proinsulin is located in the AC junction of proinsulin and des-31,32-proinsulin and includes a peptide sequence selected from:

the sequence LysArg, preferably the sequence Leu Gln Lys Arg Gly Ile Val Glu (SEQ ID NO: 3), and still more preferably, the sequence Leu Gln Lys Arg Gly Ile Val Glu Gln (SEQ ID NO: 4).

The anti-proinsulin antibody of the invention preferably inhibits at least 50% of the binding of the anti-C-peptide antibody to proinsulin when it is present in the same concentration as the anti-C-peptide antibody.

In another preferred implementation of the invention, said epitope recognised by the antibody which is specific to intact proinsulin and des-64,65-proinsulin is located in the BC junction of proinsulin and des-64,65-proinsulin and includes the peptide sequence:

Arg Arg.

Antibodies used to carry out the method of the invention may be monoclonal or polyclonal antibodies. At least one monoclonal antibody is preferably used.

Particular antibodies which are specific to des-31,32-proinsulin and proinsulin are monoclonal antibodies which recognise an epitope which is either adjacent or overlaps the epitope for the anti-C-peptide antibody, thus interfering with binding of the anti-C-peptide antibody to intact proinsulin and to des-31,32-proinsulin, said epitope being located in the AC junction of proinsulin and des-31,32-proinsulin and the sequence including a peptide sequence selected from:

Lys Arg, preferably the sequence:

Leu Gln Lys Arg Gly Ile Val Glu (SEQ ID NO: 3)

and more particularly the sequence:

Leu Gln Lys Arg Gly Ile Val Glu Gln (SEQ ID NO: 4).

The antibody can in particular be the monoclonal AC1D4 antibody obtained from a hybridoma deposited at the Collection Nationale de Cultures de Microorganismes [National Collection of Microorganism Cultures] at the Institut Pasteur on 4th Jun. 1997, registration number I-1873.

The method of the invention can use antibodies specific to des-64,65-proinsulin and proinsulin which recognise an epitope which is either adjacent or overlaps the anti-C-peptide antibody epitope, thus interfering with binding of the anti-C-peptide antibody to intact proinsulin and to des-64,65-proinsulin, said epitope being located in the BC junction of proinsulin and des-64,65-proinsulin and including the peptide sequence selected from:

the sequence Arg Arg, the sequence Phe Tyr Thr Pro Lys Thr Arg Arg Glu Ala Glu Asp Leu Gln Val (SEQ ID NO: 5).

the sequence Thr Pro Lys Thr Arg Arg Glu Ala Glu Asp Leu Gln Val (SEQ. ID NO: 2).

the sequence Phe Tyr Thr Pro Lys Thr Arg Arg Glu Ala Glu Asp Leu (SEQ. ID NO: 6).

Specific antibodies for des-64,65-proinsulin and proinsulin are preferably used which recognise an epitope corresponding to the sequences:

Thr Pro Lys Thr Arg Arg Glu Ala Glu Asp Leu Gln Val
    (SEQ ID NO: 2)
or
Phe Tyr Thr Pro Lys Thr Arg Arg Glu Ala Glu Asp Leu
    (SEQ ID NO: 6).

Clearly, when an antibody specific to intact proinsulin and des-31,32-proinsulin is used, it is possible to avoid interference due to binding of the anti-C-peptide antibody to split-32,33-proinsulin. Similarly, using an antibody specific to intact proinsulin and des-64,65-proinsulin avoids interference due to binding of the anti-C-peptide antibody to split-65,66-proinsulin.

The method of the invention can be used to assay C-peptide in biological samples such as plasma, serum or urine.

A preferred assay method in accordance with the invention is a "sandwich" type assay in which a monoclonal or polyclonal anti-C-peptide antibody can be fixed on a solid phase. The anti-C-peptide is preferably a monoclonal antibody. After bringing it into contact with the biological sample for assay, a second anti-C-peptide antibody bonded to a tracer, for example an enzyme tracer, is added. Antibodies which enable specific assay of C-peptide in accordance with the invention (in particular antibodies specific to des-31,32-proinsulin and possibly antibodies specific to des-64,65-proinsulin) can be used, either simultaneously with or before the second anti-C-peptide antibody. Assay can be carried out in one or in two stages and the C-peptide can be evaluated using any detection method, such as enzymatic detection, or detection using a radioactive, fluorescent, or chemiluminescent agent, etc.

A further type of assay which can be used in the method of the invention is "competitive" radioimmunological assay. In this type of assay, a monoclonal or polyclonal anti-C-peptide antibody, which may be bound to a solid phase, is brought into contact with a biological sample to be assayed. Then the antibody specific to des-31,32-proinsulin and/or the antibody specific to des-64,65-proinsulin is introduced, as well as C-peptide labelled with a detectable tracer such as an agent as cited above.

Kits containing an anti-C-peptide antibody and an antibody specific to des-31,32-proinsulin and proinsulin and/or an antibody specific to des-64,65-proinsulin and proinsulin also form part of the present invention. These kits enable the specific C-peptide assay method to be carried out. The kits of the invention are used either for sandwich or for competitive type specific C-peptide assay.

Production and Characterisation of AC1D4 Monoclonal Antibody:

1. Production

AC1D4 monoclonal antibody was obtained by lymphocyte hybridisation.

Six week old female Balb/c mice received a total of four intraperitoneal injections of human proinsulin. On day 1 the mice were intraperitoneally immunised with 50 μg of human proinsulin in the presence of complete Freund adjuvant. Three weeks later the mice were immunised again with 50 μg of human proinsulin in the presence of incomplete Freund adjuvant. A third immunisation was carried out three weeks later, under the same conditions as before, using a solution of human proinsulin in a phosphate buffer saline solution (PBS) at a pH of 7.4. Blood samples were taken from the mice after the second and third injections, 12 days after each injection. The serums were tested using ELISA, RIA and SPOT (Franck R. Tetrahedron, (1992), 48, p 9217–9232) for the presence of human anti-proinsulin antibodies.

Mice with a high seric anti-proinsulin antibody level were selected for lymphocyte fusion. The selected mice received a final injection of proinsulin one month after the third injection. The dose of 20 μg was injected in two aliquots. Three days later the mice were decapitated and the spleen was removed. After grinding the spleen, the lymphocytes were fused with myelomatous mouse cells from the P3-X63-Ag8.653 line in the presence of polyethylene glycol. The lymphocyte hybridisation technique used was the Clona-Cell™ technique from StemCell Technologies Inc (distributed in France by TEBU, Le Perray Yvelines). Selection of antibody-secreting hybridomas was effected by a series of tests carried out in parallel using ELISA (using immobilised human proinsulin) and RIA (using iodinated human proinsulin). The secreting hybridomas were SPOT analysed for their anti-AC or BC junction activity.

For the ELISA method, NUNC microplaques were coated with human proinsulin using 100 μl of a solution of human proinsulin (C=0.1 μg/ml) in PBS. The plates were incubated overnight at +4° C. After washing three times with a phosphate buffered saline solution with added 0.1% Tween 20 (PBS-Tween), 200 μl of supernatant culture or 100 μl of purified antibodies were deposited in decreasing concentrations in the microplaques and incubated for three hours at room temperature. The microplaques were than washed three times with PBS-Tween and a second antibody was added. This antibody, directed against mouse IgG (gamma specificity) was coupled with peroxidase and had been dissolved in PBS-Tween (dilution 1/3000). The microplaques were incubated for one hour at 37° C., then washed three times with PBS-Tw. The reaction was revealed using as a substrate orthophenyldiamine in solution (C=30 mg/ml) in a citrate buffer solution at pH=5 containing 0.03% of hydrogen peroxide. The absorbance was measured at λ=450 nm after 20 minutes incubation at room temperature and away from light. The enzymatic reaction was stopped with 50 μl of 4N sulphuric acid and the measurement was carried out at λ=490 nm.

For the RIA method, 100 μl of supernatant culture or 100 μl of purified antibody was deposited in decreasing concentrations in tubes coated with sheep anti-mouse IgG antibodies. After three hours of incubation at room temperature, the tubes were washed three times with 2 ml of PBS, after which 100 μl of iodinated proinsulin, 3000 cpm, in solution in PBS containing 1% of BSA was added. The tubes were incubated overnight at room temperature, then washed three times with PBS (2 ml/tube) and then introduced into a gamma counter for reading.

One of the hybridomas was AC1D4. This hybridoma was cloned by limit dilution (Lefkovits I and Waldmann S. 1979, Cambridge University Press, Cambridge). In this technique, the cellular suspension was diluted by tens until a solution containing five cells/ml was obtained. This solution was distributed in cell culture microplaques in a proportion of 100 μl per well. Inverted microscope examination allowed cell development to be monitored and wells with a single clone to be retained.

2. Characterisation 2.1. Antigenic Specificity

Isotype IgG1 AC1D4 antibody recognises:

human proinsulin and des-31,32-proinsulin in ELISA format (immobilised proinsulin), and human proinsulin and des-31,32-proinsulin in RIA format (iodinated proinsulin in solution).

Figure 1:
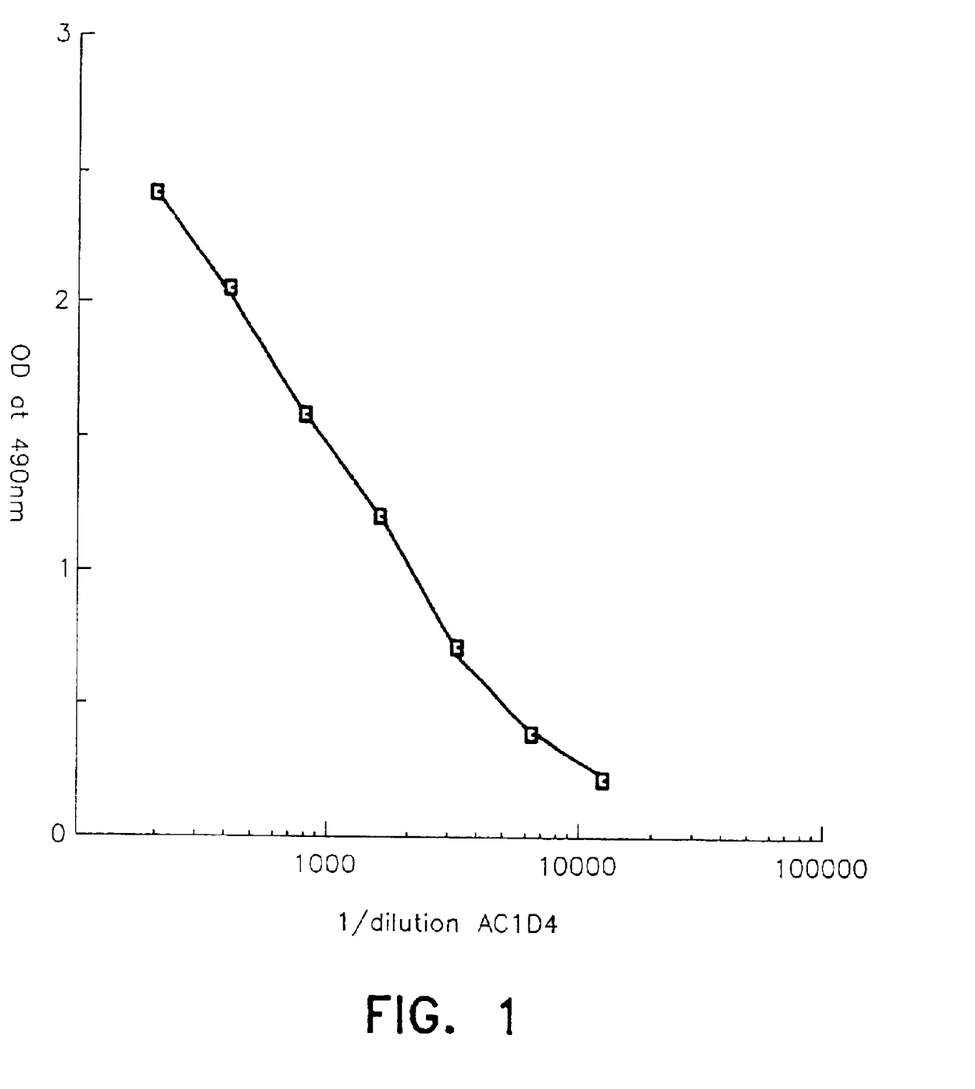
FIG. 1 shows the binding of AC1D4 antibody to proinsulin for ELISA.
Figure 2:
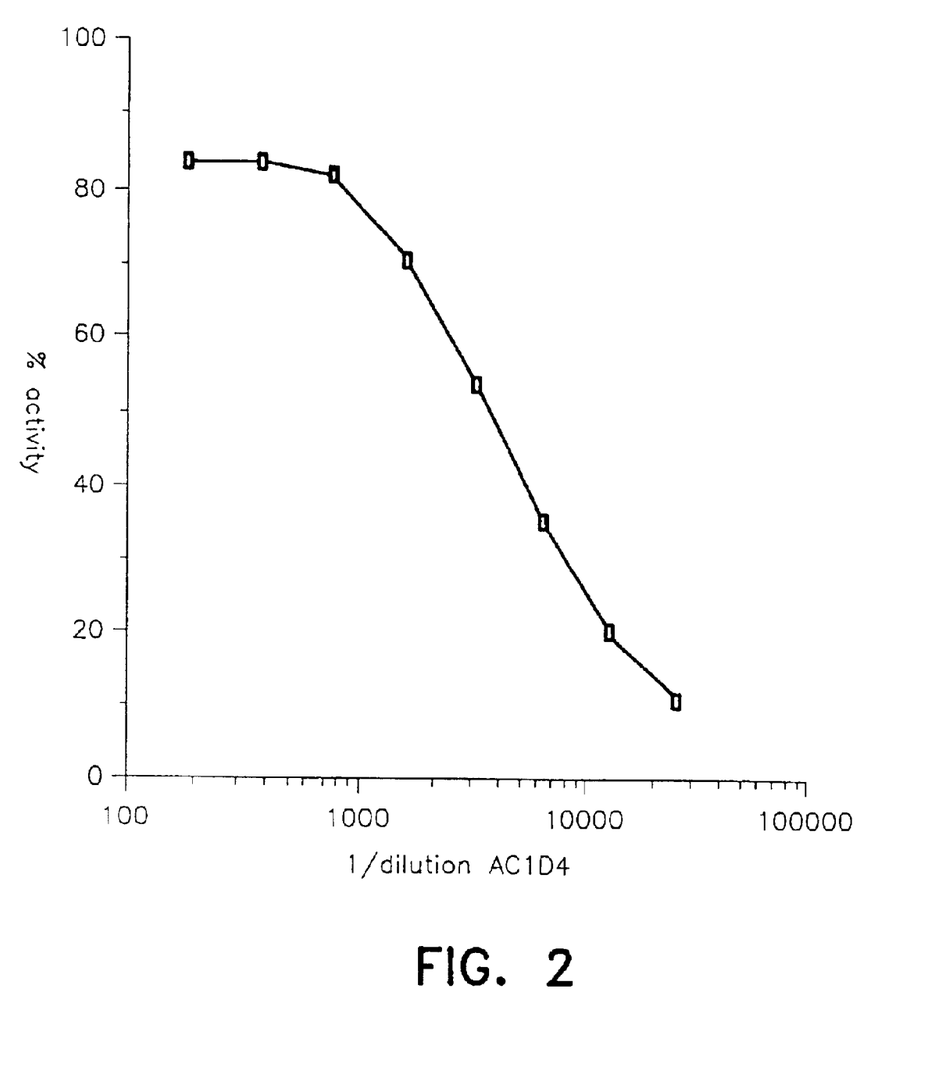
FIG. 2 shows the binding of AC1D4 antibody to labeled proinsulin for RIA.

The results of these studies are given in FIGS. 1 and 2.

FIG. 1 shows the binding of AC1D4 antibody to proinsulin for ELISA.

FIG. 2 shows the binding of AC1D4 antibody to labelled proinsulin for RIA.

2.2. Cross Reactions

Competitive tests by insulin and human C-peptide of the binding of AC1D4 antibody to iodinated human proinsulin were carried out using RIA. The experimental conditions were identical to those of the RIA method indicated above (see under Production) with the exception of the proinsulin incubation step. In the present case, after incubating the AC1D4 antibody in the tubes (followed by washing), the insulin or C-peptide, at 10 µg/ml, was incubated at the same time as the iodinated proinsulin.

The results showed that human insulin and C-peptide do not inhibit the binding of AC1D4 to iodinated proinsulin.

2.3. Assay of the Epitope Sequence

The epitope sequence was determined using SPOT?. Peptides consisting of nine amino acids overlapping eight amino acids were synthesised on a nitrocellulose membrane. The synthesised peptides thus covered the whole of the human proinsulin molecule (i.e. a total of 78 peptides). This membrane acted as an antigenic support for analysing the sequence recognised by the monoclonal antibody under test.

The following protocol was used for the immunological reaction after peptide synthesis:

The membrane was saturated in a saturation buffer containing 10% of CRB (Cambridge Research Biochemicals from GENOSYS, ref: SU-07-250), 0.5% of Tween and 5% of saccharose in TBS (Tris Buffer Saline). After one night, with stirring and at room temperature, the membrane was washed in TBS-Tween and AC1D4 antibody diluted in the saturation buffer (C=1 µg/ml) was added. The result was then incubated, with stirring, for one and a half hours at 37° C. After washing with TBS-Tween, addition of an anti-mouse IgG antibody coupled to alkaline phosphatase enabled the presence of the antibody to be studied to be revealed after incubation for one hour at room temperature and with stirring. The complex formed was visualised by adding BCIP substrate (5-bromo-4-chloro-3-indolyl phosphate toluidinium salt) containing magnesium chloride and Thiazolyl blue in a citrate buffer saline (CBS) solution.

The peptide recognised by AC1D4 antibody was the peptide with the sequence:

Leu Gln Lys Arg Gly Ile Val Glu Gln (SEQ ID NO: 4)

This sequence is located in the junction of insulin chain A and C-peptide.

2.4. Kinetic Parameters

The parameters were determined using the BIAcore™ system. This system measures the binding between an antibody and its antigen in real time. The unit of measurement is the RU, and this method enables the association rate constant (Kon), the dissociation rate constant (Koff) and finally the constant (KA) for binding of the antibody to human proinsulin to be determined. The results of this study are given in Table I.

TABLE I

| Monoclonal antibody | AC1D4 |
|---|---|
| Signal RU | 1305 |
| Koff (s$^{-1}$) | 1.65 × 10$^{-5}$ |
| Kon (M$^{-1}$ s$^{-1}$) | 1.16 × 10$^{5}$ |
| KA (M$^{-1}$) | 7 × 10$^{9}$ |

2.5. Binding of Anti-C-peptide Monoclonal Antibody to Human Proinsulin in the Presence and Absence of AC1D4 Antibody PEP001 anti-C-peptide monoclonal antibody and AC1D4 antibody were tested using the BIAcore™ system for their capacity to fix simultaneously to proinsulin coupled to dextran. The PEP001 monoclonal antibody from DAKO recognises a C-peptide epitope corresponding to the following sequence:

Pro Gly Ala Gly Ser Leu Gln Pro Leu Ala Leu Glu Gly Ser(SEQ ID NO: 1)

This epitope was adjacent the epitope recognised by AC1D4 antibody on human proinsulin.

Figure 3:
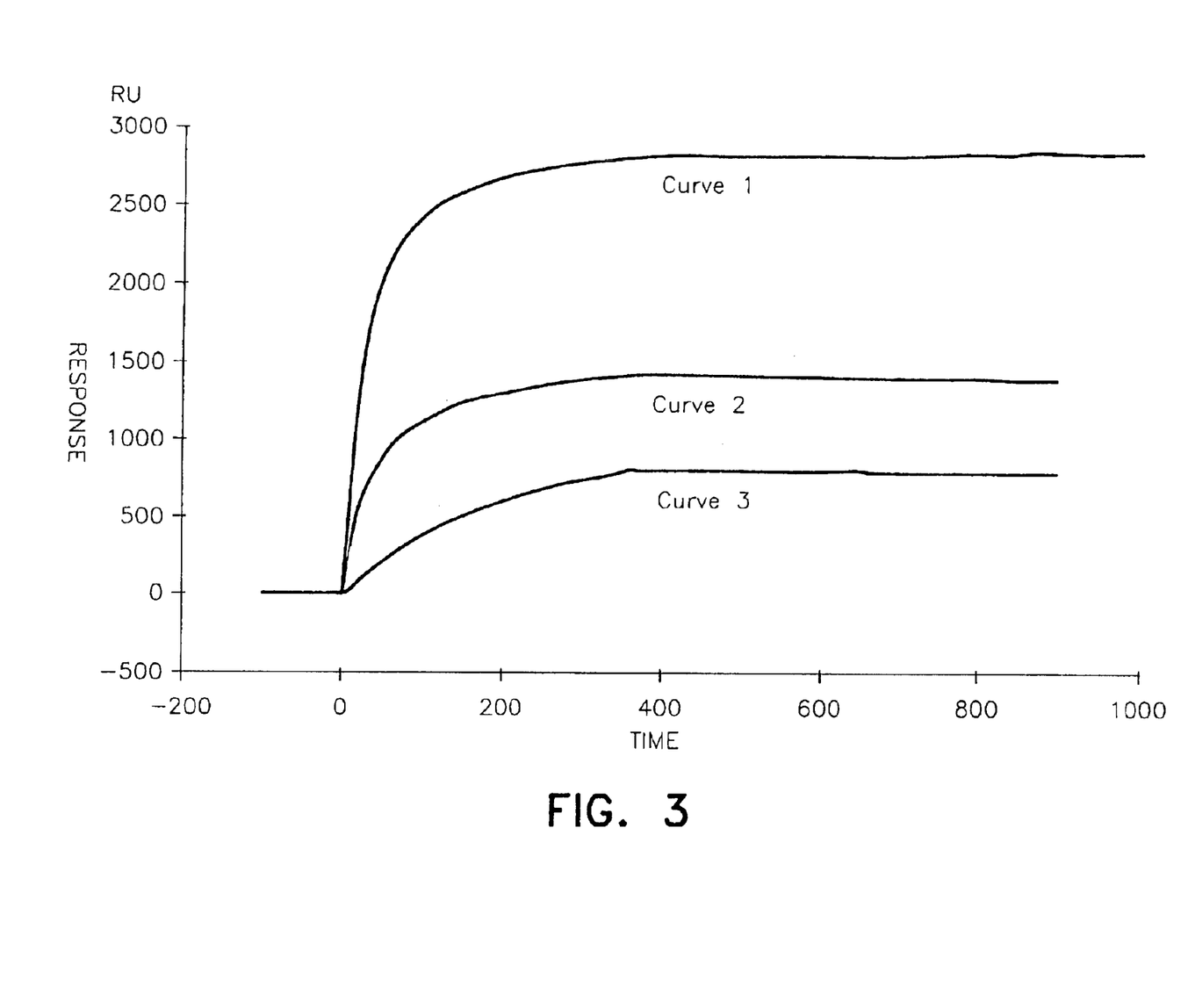
FIG. 3 shows the binding of anti-C-peptide monoclonal antibody PEP001 to human proinsulin in the absence of AC1D4 antibody (Curve 1) or in the presence of the same (Curve 2) or a ten-fold higher (Curve 3) concentration of the antibody AC1D4 antibody.

For this test, increasing quantities of AC1D4 antibody were used. The results of this study are shown in FIG. 3.

Curve 1 represents the binding of PEP001 antibody to proinsulin in the absence of AC1D4 antibody.

Curve 2 represents the binding of PEP001 antibody to proinsulin in the presence of AC1D4 antibody at the same concentration as the PEP001 antibody. In this case, a 50% inhibition of the bind of PEP001 antibody by AC1D4 antibody was observed.

Curve 3 represents the binding of PEP001 antibody to proinsulin in the presence of AC1D4 antibody at a concentration 10 times higher than that of the PEP001 antibody. In this case, a 70% inhibition of binding of PEP001 antibody by AC1D4 antibody was observed.

The following non-limiting examples illustrate the invention.

EXAMPLE 1

Specific C-peptide Assay Method in Serum. "Sandwich" Type Immunoenzymatic Assay. Evaluation of Optimum Conditions An automatic Access™ type apparatus was used to carry out this test. The test was carried out using 20 µl of serum. Two antibodies specific to proinsulin were used:

AC1D4 antibody specifically recognising proinsulin and des-31,32-proinsulin, and BC9B6 antibody specifically recognising proinsulin and des-64,65-proinsulin.

This latter antibody recognises an epitope of the BC junction corresponding to the peptide sequence:

Thr Pro Lys Thr Arg Arg Glu Ala Glu Asp Leu Gln Val (SEQ ID NO: 2)

Increasing concentrations of these antibodies were used, alone or as a mixture, to determine the concentration of AC1D4 and BC9B6 antibodies necessary to eliminate interference due to intact proinsulin, des-31,32-proinsulin and des-64,65-proinsulin.

The solid phase used was ferric latex beads (Rhône Poulenc ref. MI-070/60) on which the anti-C-peptide monoclonal antibody PEP001 was fixed by covalent binds.

The following were introduced, in order, into the reading tube:

1. 50 µl of beads coated with anti-C-peptide monoclonal antibodies,
2. 20 µl of serum previously treated with activated charcoal and into which increasing concentrations of proinsulin or des-31,32-proinsulin or des-64,65-proinsulin were introduced,
3. 80 µl of pH=8 buffer composed of 0.02 M Tris, 0.15 NaCl and preservatives, and
4. 50 µl of alkaline phosphatase conjugated with anti-C-peptide goat polyclonal antibody in a pH=8 buffer (composed of 0.1 M Tris, MgCl$_2$, 2 mM, 0.1M ZnCl$_2$, 0.15M NaCl with added protein and preservatives) and containing AC1D4 monoclonal antibody and BC9B6 monoclonal antibody at various concentrations: 0 µg/ml, 1 µg/ml, 5 µg/ml, 10 µg/ml and 20 µg/ml.

After 30 minutes incubation at 37° C., it was washed three times with pH=8 buffer (composed of 0.02M Tris, 0.15 NaCl and preservatives) and 200 µl of Lumi-Phos™ 530 substrate was added. It was incubated again for five minutes at 37° C. and the luminescence generated by the reaction was measured using a luminometer.

The results of this study are given in Tables II to IV. The results are expressed as the percentage of cross reaction.

TABLE II

| AC1D4 | 0 µg/ml | 20 µg/ml |
|---|---|---|
| Proinsulin | 92 | 8 |
| Des-31, 32-proinsulin | 108 | 16 |
| Des-64, 65-proinsulin | 94 | 85 |

TABLE III

| BC9B6 | 0 µg/ml | 20 µg/ml |
|---|---|---|
| Proinsulin | 92 | 8 |
| Des-31, 32-proinsulin | 108 | 115 |
| Des-64, 65-proinsulin | 94 | 8 |

TABLE IV

| AC1D4 + BC9B6 $Q^*_{AC1D4} = Q_{BC9B6}$ | 0 µg/ml | 2 µg/ml | 10 µg/ml | 20 µg/ml | 40 µg/ml |
|---|---|---|---|---|---|
| Proinsulin | 92 | 23 | 4 | 2 | 18 |
| Des-31,32-proinsulin | 108 | 65 | 30 | 19 | 13 |
| Des-64,65-proinsulin | 94 | 48 | 18 | 10 | 7 |

$Q^*_{AC1D4}$: quantity of AC1D4.

The results of Table IV demonstrate that adding the mixture of AC1D4 and BC9B6 antibodies each in a concentration of 20 µg/ml produces a cross reaction with proinsulin of less than 5%, a cross reaction with des-31,32-proinsulin of less than 15% and a cross reaction with des-64,65-proinsulin of less than 10%.

EXAMPLE 2

Specific C-peptide Assay Method for Urine. "Sandwich" Type Immunoenzymatic Assay In order to assay C-peptide in urine, it is possible to proceed as described in Example 1, first diluting the urine sample to 1/20th.

Adding AC1D4 antibody in a concentration of 30 µg/ml and BC9B6 in a concentration of 5 µg/ml, it is possible to obtain interference due to proinsulin of less than 5%, interference due to des-31,32-proinsulin of less than 10% and interference due to des-64,65-proinsulin of less than 20%.

EXAMPLE 3

Specific C-peptide Assay Method in Serum. Competitive Radioimmunological Assay

The assay was based on competition between a fixed quantity of tyr-C-peptide labelled with iodine ($I^{25}$) and C-peptide contained in reference solutions or in samples to be determined, for a limited number of anti-C-peptide antibody sites.

The assay was carried out using polystyrene tubes coated with PEP001 anti-C-peptide monoclonal antibody as follows:

The following was introduced into each tube:
100 µl of a standard solution containing 0.2 ng/ml to 30 ng/ml of C-peptide in solution in a pH=6.8 phosphate buffer solution with added proteins and containing 0.1% of sodium nitride or 100 µl of the sample to be assayed, and 50 µl of a solution containing monoiodinated Tyr-C-peptide diluted in a phosphate buffer containing 0.1% of sodium nitride and AC1D4 antibody specifically directed against the AC junction of the proinsulin molecule, in an amount of 20 µg/ml.

The tubes were covered with Parafilm™. After incubating for two hours at room temperature and with horizontal stirring, the reaction medium was eliminated by aspiration and washing was carried out with 2 ml of a pH=7.4 buffer solution containing 0.05 M imidazole, 0.0025% sodium azide and preservatives. This solution was eliminated by aspiration and the washing was repeated two more times.

The radioactivity of each tube was determined using a gamma scintillator adjusted to measure $I^{125}$. Counting was carried out over one minute.

The quantity of C-peptide was evaluated with respect to a reference scale. The limit of detection of this method was 0.15 ng/ml.

In order to evaluate the specificity of this assay, two serums in different concentrations were overloaded with proinsulin, des-31,32-proinsulin and des-64,65-proinsulin.

The test was carried out in the presence and in the absence of AC1D4 antibodies (C=20 µg/ml). The results of this test are shown in Tables V to VII.

TABLE V

SERUMS OVERLOADED WITH PROINSULIN

| | | No AC1D4 antibody | | With AC1D4 antibody | |
|---|---|---|---|---|---|
| Serum | Overload (pmol/ml) | Value found (pmol/ml) | Increase after overload (%) | Value found (pmol/ml) | Increase after overload (%) |
| E1 | 0 | 0.628 | — | 0.621 | — |
| | 0.16 | 0.721 | 15 | 0.587 | 0 |
| | 0.67 | 0.980 | 56 | 0.659 | 6 |
| | 3.33 | 2.437 | 288 | 0.811 | 31 |
| E2 | 0 | 2.998 | — | 3.33 | — |
| | 0.16 | 3.040 | 1 | 3.17 | 0 |
| | 0.67 | 3.363 | 12 | 3.35 | 1 |
| | 3.33 | 4.622 | 54 | 3.14 | 0 |

TABLE VI

SERUMS OVERLOADED WITH DES-31,32-PROINSULIN

| | | No AC1D4 antibody | | With AC1D4 antibody | |
|---|---|---|---|---|---|
| Serum | Overload (pmol/ml) | Value found (pmol/ml) | Increase after overload (%) | Value found (pmol/ml) | Increase after overload (%) |
| E1 | 0 | 0.593 | — | 0.577 | — |
| | 0.16 | 0.640 | 8 | 0.606 | 5 |
| | 0.67 | 0.819 | 38 | 0.646 | 12 |
| | 3.33 | 1.858 | 213 | 0.700 | 21 |
| E2 | 0 | 2.490 | — | 2.41 | — |
| | 0.16 | 2.730 | 10 | 2.35 | 0 |
| | 0.67 | 2.700 | 8 | 2.52 | 5 |
| | 3.33 | 3.971 | 59 | 2.56 | 6 |

TABLE VII

SERUMS OVERLOADED WITH DES-64,65-PROINSULIN

| Serum | Overload (pmol/ml) | No AC1D4 antibody | | With AC1D4 antibody | |
|---|---|---|---|---|---|
| | | Value found (pmol/ml) | Increase after overload (%) | Value found (pmol/ml) | Increase after overload (%) |
| E1 | 0 | 0.494 | — | 0.552 | — |
| | 0.16 | 0.523 | 6 | 0.608 | 10 |
| | 0.67 | 0.734 | 49 | 0.900 | 63 |
| | 3.33 | 1.815 | 267 | 1.887 | 242 |
| E2 | 0 | 2.401 | — | 2.25 | — |
| | 0.16 | 2.410 | 0 | 2.24 | 0 |
| | 0.67 | 2.614 | 9 | 2.66 | 18 |
| | 3.33 | 3.715 | 55 | 3.80 | 69 |

The results of this study demonstrate that the presence of a monoclonal antibody specific to the AC junction in proinsulin can eliminate interference due to proinsulin and des-31,32-proinsulin in assaying C-peptide using PEP001 antibody, the epitope of which is close to that of AC1D4.

What is claimed is:

1. A method for assaying C-peptide in a sample suspected of containing C-peptide, intact proinsulin, des-31,32 proinsulin, and/or des-64,65-proinsulin comprising:
   a) contacting the sample with at least a first anti-peptide antibody which specifically binds an epitope present entirely in the C-peptide and a second antibody which is selected from:
      an anti-proinsulin antibody which is specific to intact proinsulin and des-31,32-proinsulin and recognizes an epitope located in an intact A-chain-C-peptide (AC) junction of proinsulin and des-31,32 proinsulin, said anti-proinsulin AC junction antibody epitope being either adjacent to or overlapping with the epitope of said at least one anti-C-peptide antibody, or
      an anti-proinsulin antibody which is specific to intact proinsulin and des-64,65-proinsulin and recognizes an epitope located in an intact B-chain-C-peptide (BC) junction of proinsulin and des-64,65-proinsulin, said anti-proinsulin BC junction antibody epitope being either adjacent to or overlapping with the epitope of said at least one anti-C-peptide antibody, or
      a mixture of said anti-proinsulin AC junction antibody and said anti-proinsulin BC junction antibody under conditions such that said at least one anti-C-peptide antibody binds to C-peptide in the sample, binding of the anti-proinsulin AC junction antibody to any proinsulin and/or des-31,32-proinsulin interferes with binding of said at least one anti-C-peptide antibody to intact proinsulin and des-31,32-proinsulin in the sample, and/or binding of the anti-proinsulin BC junction antibody to any proinsulin and/or des-64,65-proinsulin interferes with binding of said at least one anti-C-peptide antibody to intact proinsulin and des-64,65-proinsulin in the sample; and
   b) detecting amount of C-peptide bound to said at least one anti-C-peptide antibody in said contacted sample as an assay of the amount of C-peptide in the sample.

2. The method according to claim 1, wherein said epitope located in the AC junction of proinsulin and des-31,32-proinsulin includes a peptide sequence: Lys Arg.

3. The method according to claim 1, wherein said epitope located in the AC junction of proinsulin and des-31,32-proinsulin includes a peptide sequence:
   Leu Gln Lys Arg Gly Ile Val Glu (SEQ ID NO: 3).

4. The method according to claim 1, wherein said epitope located in the AC junction of proinsulin and des-31,32-proinsulin includes a peptide sequence:
   Leu Gln Lys Arg Gly Ile Val Glu Gln (SEQ ID NO: 4).

5. The method according to claim 1, wherein said epitope located in the BC junction of proinsulin and des-64,65-proinsulin includes a peptide sequence: Arg Arg.

6. The method according to claim 1, wherein the sequence of said epitope located in the BC junction of proinsulin and des-64,65-proinsulin is selected from the group consisting of:
   Phe Tyr Thr Pro Lys Thr Arg Arg Glu Ala Glu Asp Leu Gln Val (SEQ ID NO: 5)
   Thr Pro Lys Thr Arg Arg Glu Ala Glu Asp Leu Gln Val (SEQ ID NO: 2); and
   Phe Tyr Thr Pro Lys Thr Arg Arg Glu Ala Glu Asp Leu (SEQ ID NO: 6).

7. The method according to claim 1 comprising:
   a) contacting the sample with the anti-C-peptide antibody and an anti-proinsulin antibody which is specific to intact proinsulin and des-31,32-proinsulin and recognizes an epitope located in the AC junction of proinsulin and des-31,32-proinsulin, said proinsulin AC junction epitope either being adjacent or overlapping the epitope of said anti-C-peptide antibody, thus interfering with binding of the anti-C-peptide antibody to intact proinsulin and des-31,32-proinsulin and b) detecting the amount of C-peptide bound to said anti-C-peptide antibody.

8. The method according to claim 1 comprising:

a) contacting the sample with the anti-C-peptide antibody and an anti-proinsulin antibody which is specific to intact proinsulin and des-64,65-proinsulin and recognizes an epitope located in the BC junction of proinsulin and des-64,65-proinsulin, said proinsulin BC junction epitope either being adjacent or overlapping the epitope of said anti-C-peptide antibody, thus interfering with binding of the anti-C-peptide antibody to intact proinsulin and des-64,65-proinsulin and b) detecting the amount of C-peptide bound to said anti-C-peptide antibody.

9. The method according to claim 1 in which at least one of said antibodies is a monoclonal antibody.

10. The method according to claim 1 in which the sample is obtained from serum, plasma, or urine.

11. The method according to claim 1, said method being a sandwich assay.

12. The method according to claim 1, said method being a competitive radioimmunological assay.

* * * * *